(12) United States Patent
Wind (10) Patent No.: US 11,938,237 B1
(45) Date of Patent: Mar. 26, 2024

(54) UTENSIL SANITIZER

(71) Applicant: Brian E. Wind, North Canton, OH (US)

(72) Inventor: Brian E. Wind, North Canton, OH (US)

( * ) Notice: Subject to any disclaimer, the term of this patent is extended or adjusted under 35 U.S.C. 154(b) by 845 days.

(21) Appl. No.: 17/011,807

(22) Filed: Sep. 3, 2020

(51) Int. Cl.
| | | |
|---|---|---|
| *A61L 2/10* | (2006.01) | |
| *A47F 1/10* | (2006.01) | |
| *G07F 11/04* | (2006.01) | |
| *G07F 11/72* | (2006.01) | |

(52) U.S. Cl.
CPC ............... *A61L 2/10* (2013.01); *A47F 1/10* (2013.01); *G07F 11/04* (2013.01); *G07F 11/72* (2013.01); *A61L 2202/11* (2013.01)

(58) Field of Classification Search
CPC .......... A47F 1/10; A61L 2/10; A61L 2202/11; G07F 11/04; G07F 11/72
USPC .......................................... 312/42; 221/76–86
See application file for complete search history.

(56) References Cited

U.S. PATENT DOCUMENTS

| | | | | | |
|---|---|---|---|---|---|
| 5,535,916 | A * | 7/1996 | Veltman | ............... | A23L 3/06 221/76 |
| 6,039,928 | A * | 3/2000 | Roberts | ............... | A61L 2/10 422/186.3 |
| 6,786,357 | B2 * | 9/2004 | Renard | ............... | G07F 11/24 221/277 |
| 7,325,700 | B1 * | 2/2008 | Masten | ............... | A47F 1/10 221/265 |
| 7,642,524 | B1 * | 1/2010 | Alvarez | ............... | A61L 2/202 250/455.11 |
| 7,646,000 | B2 * | 1/2010 | Shih | ............... | A61L 2/10 250/455.11 |
| 8,058,629 | B2 * | 11/2011 | Long | ............... | A61L 2/10 250/455.11 |
| 8,172,072 | B2 * | 5/2012 | Hirata | ............... | G01N 35/04 198/562 |
| 8,337,770 | B2 * | 12/2012 | Wind | ............... | A61L 2/10 250/455.11 |
| 8,357,914 | B1 * | 1/2013 | Caldwell | ............... | A61L 2/10 250/455.11 |
| 9,345,799 | B1 * | 5/2016 | Wind | ............... | B43K 23/02 |
| 10,595,647 | B2 * | 3/2020 | Erickson | ............... | A47F 1/10 |
| 10,806,813 | B1 * | 10/2020 | Wind | ............... | A61L 2/10 |
| 11,097,027 | B2 * | 8/2021 | Erwin | ............... | B43K 23/002 |
| 11,116,857 | B1 * | 9/2021 | Benin | ............... | A61L 2/24 |

* cited by examiner

*Primary Examiner* — Daniel J Troy
*Assistant Examiner* — Timothy M Ayres
(74) *Attorney, Agent, or Firm* — Robert R. Lech; Lech Law, LLC (57) ABSTRACT

A sanitizer and a method for using a sanitizer are disclosed. The sanitizer comprises an illumination source, a collection frame, a discharge frame and a carrier system comprising a pair of belts to transport the elongated item between the collection frame and the discharge frame. The elongated item may be a writing instrument, a stylus, an eating utensil, or any other elongated object.

15 Claims, 6 Drawing Sheets

UTENSIL SANITIZER

TECHNICAL FIELD

The present application relates generally to sanitization and dispensing devices for handheld elongated implements such as eating utensils and writing utensils, and more particularly to an ultraviolet (UV) light sanitizer including a receiving and dispensing mechanism compatible with elongated implements of various and/or irregular shapes.

STATEMENT REGARDING FEDERALLY SPONSORED RESEARCH

No government monies were used in the development of the subject matter of this application.

BACKGROUND

When humans are exposed, microorganisms, such as bacteria, fungi, archaea and protists, and viruses, such as influenza and coronavirus, can cause serious illness. Restaurants often provide eating utensils to both dine-in and carryout patrons for consuming their food. If improperly cleaned, infectious microorganisms can colonize on such eating utensils and promote the spread of communicable diseases from the common cold to more serious infections.

Similarly, hand-held writing utensils are commonly utilized and shared by individuals in public places such as hospitals, doctor's offices, banks, department stores, and restaurants. Improperly cleaned writing utensils can also promote the spread of communicable diseases. The use of ultraviolet light for its purification and germicidal effects is well known. When administered at the desired frequencies, durations, and intensities, ultraviolet light is able to kill a wide spectrum of microorganisms.

While prior art sanitization devices are known, no known device is configured to sanitize and dispense eating utensils. Further, prior art mechanisms for dispensing sanitized articles typically require the user to affirmatively request a sanitized article. Accordingly, there is a need for an improved sanitization device that is configured to sanitize and dispense eating utensils. There is a further need for an improved sanitization device that automatically dispenses sanitized articles when needed by a user without requiring a user to input a request.

BRIEF DESCRIPTION OF THE DRAWINGS

The accompanying figures, which are incorporated in and constitute a part of the specification, illustrate various example systems, devices methods, and so on, and are used merely to illustrate various example embodiments. Like reference numerals refer to identical or similar components or steps. It should be noted that the various components depicted in the figures may not be drawn to scale, and that the various assemblies and designs depicted in the figures are presented for purposes of illustration only, and should not be considered in any way as limiting.

DRAWING REFERENCE NUMERALS

The following reference characters identify the associated elements depicted in the drawings describing the present invention:

| Ref. | Element |
| --- | --- |
| 100 | First Example Sanitizer |
| 102a | Inserted Writing Utensil |
| 102b | Discharged Writing Utensil |
| 110 | Housing |
| 111 | Front Housing Element |
| 112 | Rear Housing Element |
| 113 | Bottom Housing Element |
| 114 | Top Housing Element |
| 115 | Window |
| 116 | Left Frame Element |
| 117 | Right Frame Element |
| 118 | Bottom Cover Plate |
| 119 | Heat Sink |
| 120 | Left Structural Support |
| 121 | Right Structural Support |
| 122 | Battery Cover Plate |
| 123 | LED array with Reflector |
| 125 | Implement Receiver |
| 126 | Left Bearing |
| 127 | Receiver Axle |
| 128 | Right Bearing |
| 129 | Receiver Drive Gear |
| 130 | Drive Motor Assembly |
| 132 | Batteries |
| 138 | Discharge Opening |
| 140 | Discharge Frame |
| 150 | Collection opening |
| 162 | Left Belt |
| 164 | Right Belt |
| 166 | Left Implement Holder |
| 168 | Right Implement Holder |
| 170 | Left Rotation Belt |
| 172 | Right Rotation Belt |
| 400 | Second Example Sanitizer |
| 410 | Integrated POS Device |
| 500 | Third Example Sanitizer |
| 510 | Separate POS Device |
| 512 | Cable |
| 600 | Control Circuit |
| 610 | Input Switch |
| 612 | Activation Mechanism |
| 614 | Illumination Switch |
| 616 | Safety Sensor |
| 618 | Contaminant Sensor |
| 620 | Processor |
| 622 | Timer |
| 624 | Optional Display |
| 626 | Optional Speaker |
| 628 | Power Supply |
| 630 | Light Source |

DETAILED DESCRIPTION OF EMBODIMENTS OF THE INVENTION

Particular embodiments of the present devices, systems, and methods will now be described in greater detail with reference to the figures. Like reference numerals apply to similar parts throughout the several views.

Figure 1:
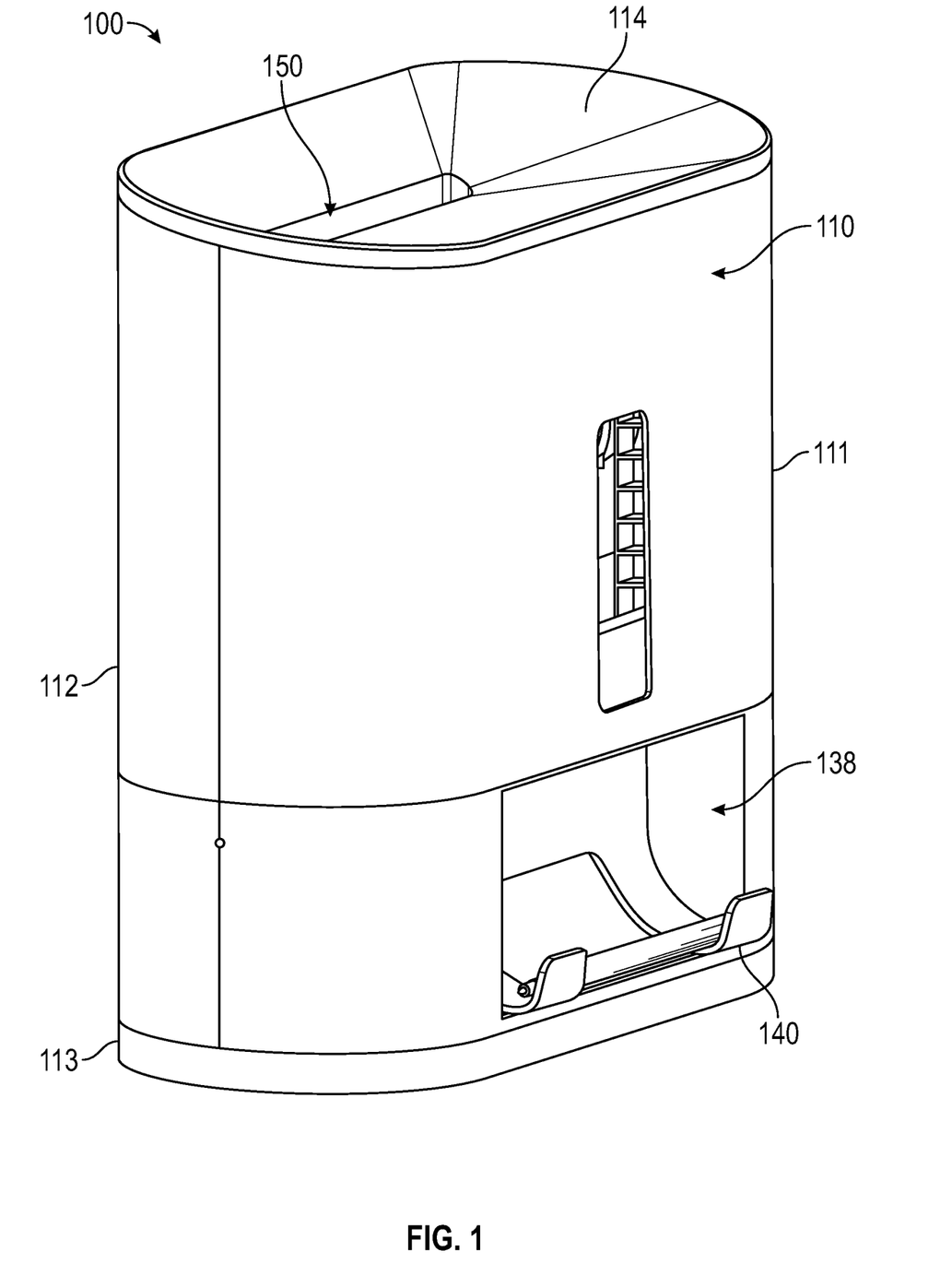
FIG. 1 illustrates a perspective view of a first example sanitizer system in accordance with this application.
Figure 2:
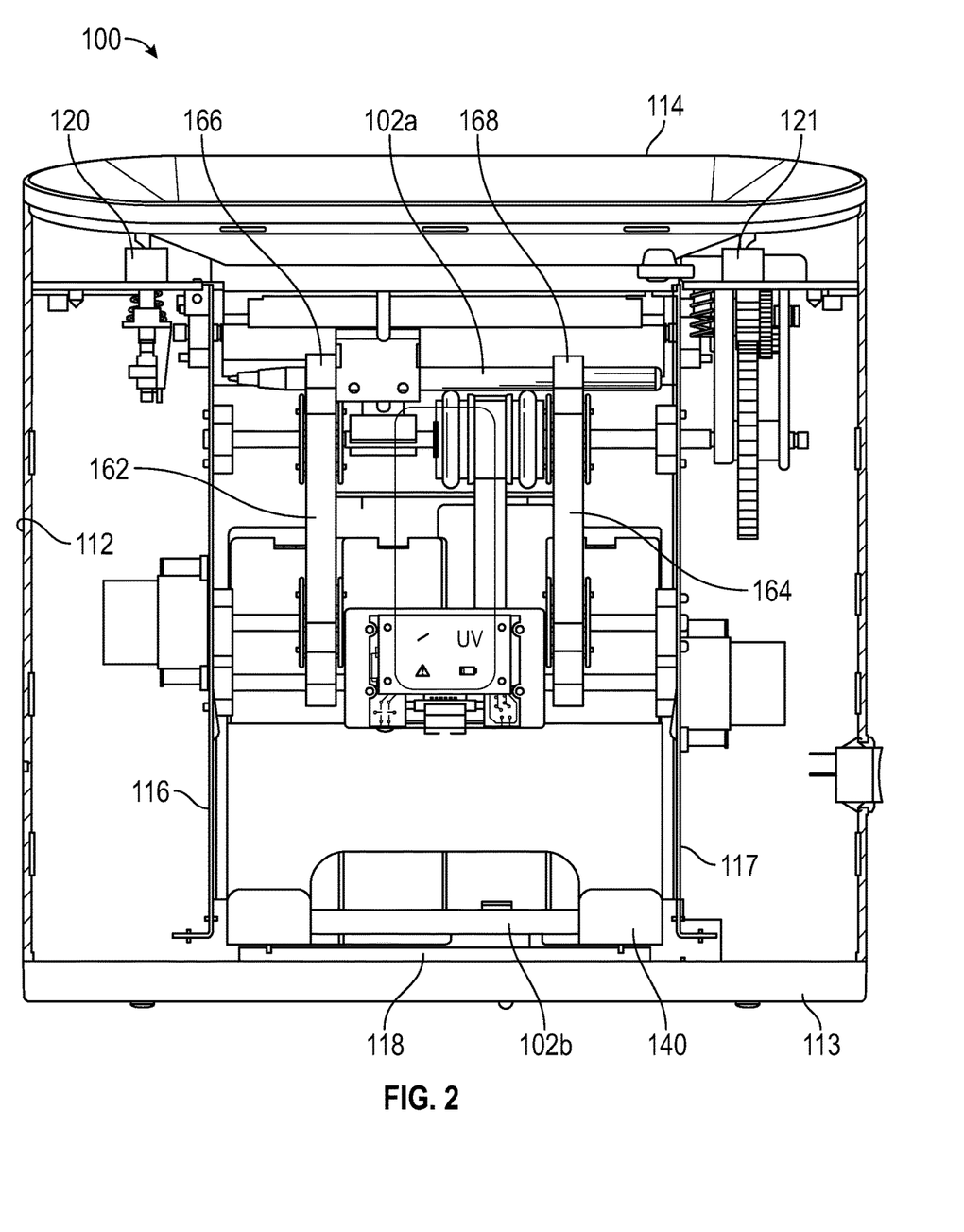
FIG. 2 illustrates a cutaway front view of the example sanitizer system of FIG. 1.
Figure 3:
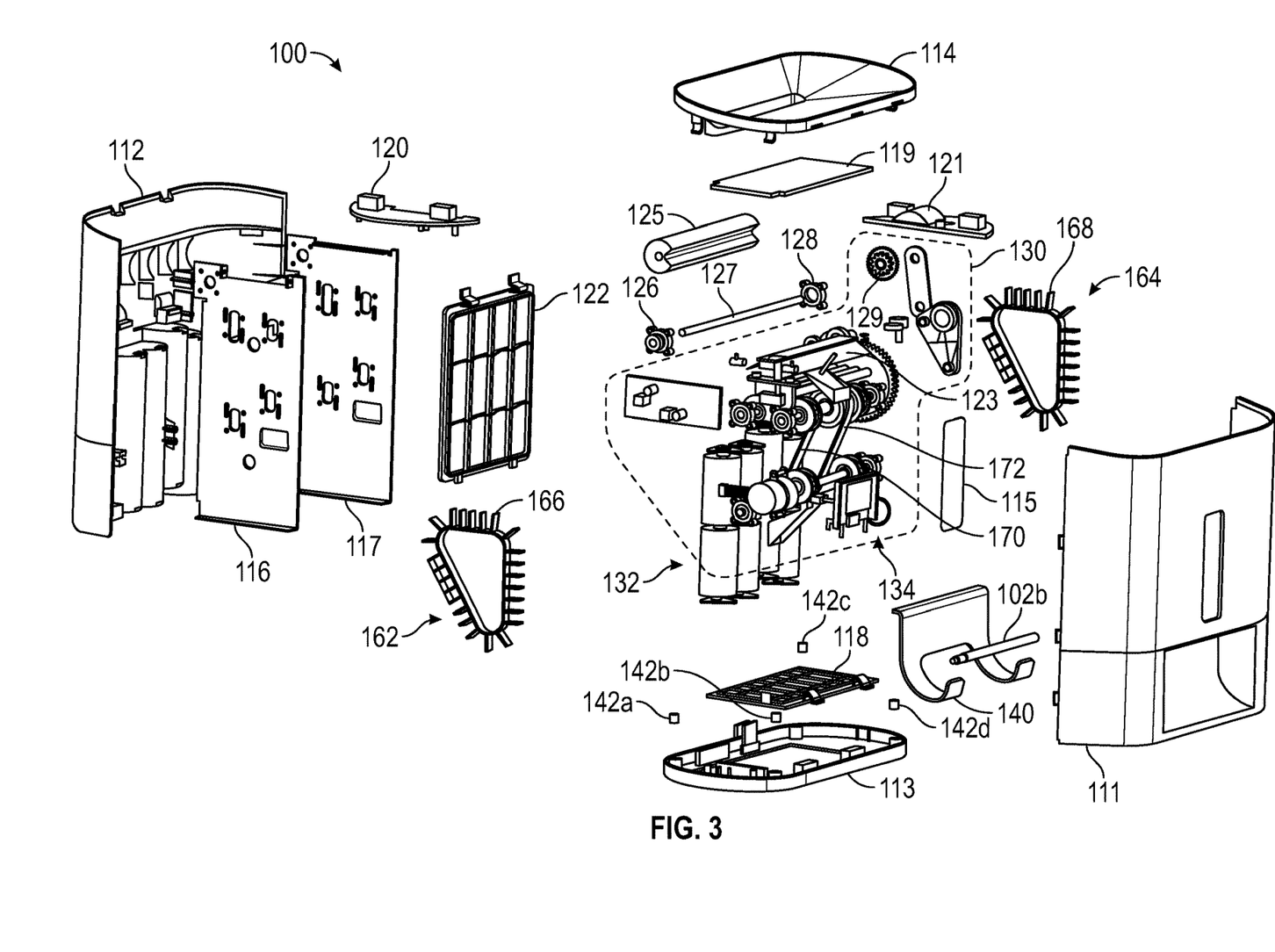
FIG. 3 illustrates an exploded view of the example sanitizer system of FIG. 1.

FIGS. 1-3 illustrate a first example sanitizer system 100 for sanitizing elongated implements. Such elongated implements may include eating utensils, such as single or attached pairs of chopsticks. Such elongated implements may further include writing utensils. For purposes of simplicity, the invention will be described with respect to writing utensils, such as, for example, example writing utensils 102*a* and 102*b* shown in FIG. 2. Of course, one of ordinary skill in the art will recognize that sanitizer 100 would work equally well with respect to eating utensils, such as chopsticks, with little or no modification.

FIG. 1 depicts an exterior, perspective view of first example sanitizer 100. FIG. 2 depicts a front cutaway view of sanitizer 100 showing the interior components of the sanitizer. FIG. 3 depicts an exploded perspective view of sanitizer 100 to further illustrate its interior components.

Sanitizer 100 comprises a housing 110, including front housing element 111, rear housing element 112, bottom housing element 113, and top housing element 114. The top housing element 114 of sanitizer 100 is a collection frame that defines a collection opening 150 for receiving an elongated object such as writing utensil 102*a* shown in FIG. 2. The front housing element 111 of sanitizer 100 defines a discharge opening 138 which provides access to a discharge frame 140 for dispensing an elongated object such as writing utensil 102*b*. The constituent elements of housing 100 are assembled using and held together by left structural support 120, right structural support 121, and connector tabs 142*a*-142*d* shown in FIG. 3.

The interior of sanitizer 100 preferably comprises reflective material to reflect and distribute UV light. For example, the interior surfaces of elements 111-114 of housing 100 may comprise a lining such as, a metallic laminate and/or any other material having suitable reflective properties to reflect UV light.

In the illustrated example embodiment, sanitizer 100 comprises reflector 123 which partially surrounds a UV light source (not shown). Reflector 123 operates to reflect irradiating light from the light source toward the surfaces of any writing utensils housed in sanitizer 100 in order to maximize the exposure of the various writing utensils to the sanitizing effects of UV light. Sanitizer 100 further comprises several internal structural components, including left frame element 116, right frame element 117, and bottom cover plate 118. Heat sink 119 is disposed above reflector 123 and below collection opening 150 so as to dissipate heat generated by the UV light source and radiated from reflector 123

As illustrated in FIG. 3, writing utensil sanitizer 100 comprises an implement receiver 125 disposed below the collection opening 150 of top frame element 114. Instrument receiver 125 is generally cylindrical with a notch formed in the exterior surface along its longitudinal axis. Instrument receiver 125 may be mounted on an axle 127 which is rotatably mounted through and between a left bearing 126 and a right bearing 128. A drive gear 129 is affixed to the right end of axle 127 such that rotation of drive gear 129 will also rotate axle 127.

In operation, drive gear 129 may be driven by a drive motor assembly 130. Drive motor assembly 130 is also operative to drive two belts, a left belt 162 and a right belt 164. Left and right belts 162 and 164 each comprise a plurality of corresponding, aligned implement holders, such as holders 166 and 168, for carrying an implement during the sanitization process. In one alternate embodiment, holders 166 and 168 are generally U-shaped to enable cradling a writing utensil as it is transported from the feeding position to an exit position. Drive motor assembly 130 is further operative to drive left and right rotation belts 170 and 172. At least a portion of the rotation belts 170 and 172 is disposed between and above drive belts 166 and 168 such that belts 170 and 172 lift and rotate any implements as they are carried by belts 162 and 164 in holders 166 and 168. The operation of rotation belts 170 and 172 to rotate implements being transported within sterilizer 100 ensures that all portions of the exterior surfaces of the implements are exposed to the irradiating UV light. The inner structure of sanitizer 100 is designed to sanitize four (4) writing utensils at once as they travel along the uppermost horizontal portion of belts 162 and 164.

The operation of example sanitizer 100 will now be described with general reference to FIGS. 1-3. To begin the operation, a user places a writing utensil on top housing element 114. The contour of top housing element 114 causes the writing utensil to be gravity fed through collection opening 150 and into the notch defined by implement receiver 125. If there are fewer than four (4) writing utensils already in sanitizer 100, implement receiver 125 is disposed such that the notch is facing upward, thereby being disposed to accept a new writing utensil to be sanitized. If there are already four (4) writing utensils present in sanitizer 100, implement receiver 125 will be rotated so that a smooth portion of the cylindrical wall of implement receiver 125 is facing upward. In this configuration, sanitizer 100 is unable to accept an additional writing utensil to be sanitized. There are a number of design choices that may accomplish the above-described functionality, including employing a counter or a writing utensil sensor, for example. Referring now to FIG. 2, writing utensil 102*a* is illustrated in the described receiving position.

Upon receiving a writing utensil, the drive motor assembly 130 engages to rotate drive gear 129 and belts 162 and 164. The operation of drive motor assembly 130 causes implement receiver 125 to rotate in a direction toward the front of sanitizer 100, and belts 162 and 164 to rotate toward the front of sanitizer 100. The drive motor assembly 130 further rotates belts 170 and 172 so as to rotate the enclosed writing utensils for complete sanitization. The rotation of implement receiver 125 causes the retained writing utensil to roll onto an uppermost pair of implement holders, such as 166 and 168. Once in the sanitizing chamber the writing utensils are rotated by the rotation belts 170 and 172, as described above. Unlike prior art sanitation devices, the design of the present invention accommodates elongated items of various profiles, not just generally cylindrical items.

When a writing utensil is requested by a user, the drive motor assembly 130 causes writing utensils resting on implement holders to be carried along the horizontal portion of the guide path defined by belts 162 and 164. Once a writing utensil is in a position immediately above the top of dispenser frame 140, gravity and the backward angle of the guide path causes the writing utensil to become dislodged from its implement holders and drop into the bottom of the discharge frame 140 where a user can retrieve it. Sanitizer 100 may receive a request for a writing utensil in a variety of ways. In one embodiment, sanitizer 100 may comprise a motion sensor that a user may activate without touching a non-sanitized surface. In another embodiment, sanitizer 100 may receive a signal from another component or device, such as a point-of-sale device, as described in greater detail below.

As shown, writing utensil sanitizer 100 comprises a discharge frame 142 that forms a discharge opening 140. Discharge opening 140 defines an elongated shaped aperture through which a sanitized writing utensil may be dispensed. Discharge frame 142 receives a sanitized writing utensil upon request thereby providing a sanitized writing utensil in the discharge opening 140.

As illustrated in FIGS. 1 and 2, sanitizer 100 comprises a UV light source provided to sanitize the writing utensils. Although a single UV light may be used, it is advantageous to employ a plurality of UV lights within sanitizer 100. UV radiation is a form of electromagnetic radiation that contains measurable wavelengths in the 100-400 nanometer range. UV radiation is a well-known sanitization agent. The ultraviolet light is effective at eradicating bacteria, viruses and other pathogens. The exposure to UV light necessary to kill bacteria (or the "kill" factor) is a product of time and intensity. Suitable wavelengths for sanitizing a writing utensil are in the range of 200-300 nanometers. The ideal UV germicidal wavelength is approximately 254 to 270 nanometers.

However, it is also understood that exposure to UV light at an intensity necessary for effective and efficient eradication or sanitization of pathogenic agents is harmful to the human body so appropriate protective shielding is utilized within the dispenser to prevent direct or reflected UV light from striking the human body. The UV radiation required to effectively eradicate most pathogenic agents will be an intensity ranging from 1000-100,000 microwatts/cm2 with an ideal range of 3,000-10,000 microwatts/cm2. The object of this invention is to effectively eradicate pathogens or micro-organisms by exposing all surfaces of the writing utensil to direct (or reflected) exposure or contact with the UV radiation for a sufficient period of time. According to this exemplary embodiment, a predetermined time period for applying UV radiation to effectively sanitize the writing utensils has been calculated in the range of 30-240 seconds. Ideally, the UV radiation exposure time period when using a UV light with a wavelength of approximately 254-265 nanometers at an intensity of 10,000 microwatts/cm2 is in the range of 80-110 seconds. However, the time may vary based on the internal surface area, the internal reflective material used, and the radiation level and/or wattage output of the UV light source 630.

Various types of illumination lamps may be employed, such as for example, an UV light, a pulsed or flashed UV light, a germicidal UV flash light or LED (light emitting diodes), pulsed UV and/or any other disinfecting illumination source now known or later discovered in accordance with this invention. Ideally, the present invention will include UV LEDs which produce UV-C light germicidal wavelengths of approximately 265 nanometers.

Figure 6:
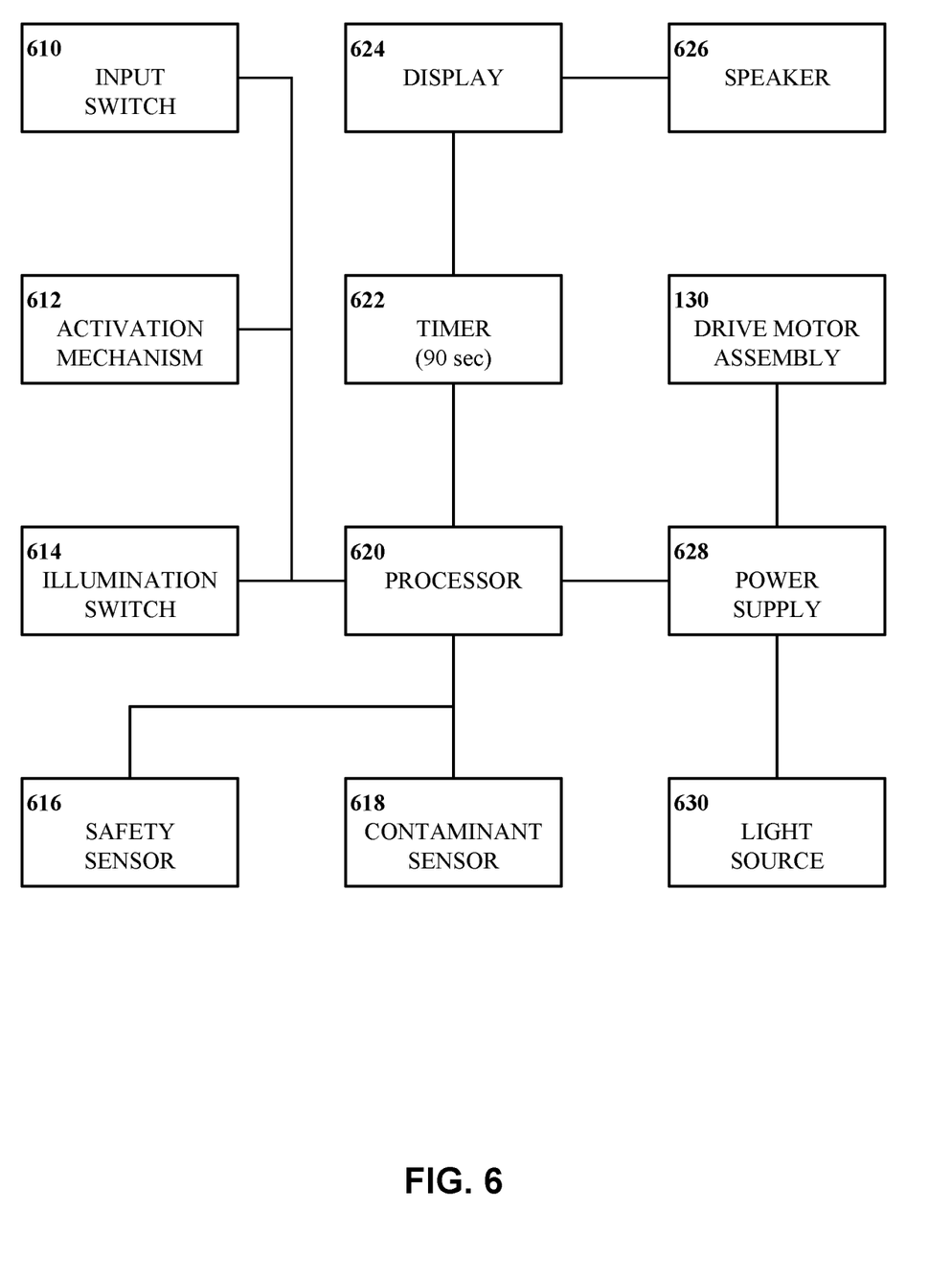
FIG. 6 illustrates a control circuit for the example sanitizers in accordance with this application.

FIG. 6 illustrates a control circuit for the example sanitizer 100 according to this application. In operation, a user may insert a writing utensil such as writing utensil 102a into the collection opening 150. An input switch 610 may be located at the opening of the collection opening 150. When the writing utensil 102a is inserted into the collection opening 150, a processor 620 receives a signal indicating the receipt of a new writing utensil 102a. The processor 620 transmits a control signal to the power supply 628 to provide a source of power to the UV light source 630 thereby allowing the various writing utensils within the sanitizer 100 to be sanitized by the irradiating UV light generated by light source 630.

Within the control circuit, sanitizer 100 may include a timer 622 to measure a predetermined period of time during which the UV light source 630 causes UV light to irradiate the writing utensil 102a. A preferred predetermined period of time has been determined to be approximately 90 seconds in accordance with this exemplary embodiment. However, it is to be understood that the predetermined time may vary based on a variety of different parameters, such as the size and number of UV light sources, the size of the housing, the reflective properties of the inner housing surfaces, the writing utensils within the housing 110 and/or other variables.

The timer 622 may be connected to an optional display 624 or an optional speaker 626. When the writing utensil 102a has been sufficiently sanitized a visual notification may be displayed on display 624 and/or an audible sound may be emitted through a speaker 626 indicating to the user that the sanitization process is complete.

The writing utensil sanitizer 100 may be connected to a contaminant sensor 618 which senses and determines whether the writing utensil 102a is sufficiently sanitized. If the contaminant sensor 618 indicates that the writing instruments 102a are not sufficiently clean, the processor 620 will continue to instruct the power supply 628 to activate the UV light source 630 until the contaminant sensor 618 detects and indicates a sanitized environment.

In more detail, the contaminant sensor 618 may be used to determine properties of the surface to be treated. Information of interest can include surface type, hardness, texture, reflectivity, and/or the extent of dirt and/or contaminants. Various other sensors, such as optical sensors, contact sensors, can be used to gather the information. The control circuit can give an indication of the surface properties and the information from the contaminant sensor 618 can be communicated to the processor 620 and used in a pre-programmed algorithm to adjust the UV intensity to be specifically tuned for the surface being treated. In the alternative, it may indicate that the intensity of UV light source 630 should be increased or reduced.

The writing utensil sanitizer 100 may include safety sensors and interlocks (hereafter safety sensor 616) that shut off the UV light source 630 when an unsafe condition is detected. An unsafe condition may include where a UV light source 630 is directed away from the treatment surface and/or in directions where it can irradiate people or animals. If an unsafe situation should occur, the processor 620 will receive control signals from the safety sensor 616 noting the harmful environment, and the processor 620 will instruct the power supply 628 to cease its supply of power to the UV light source 630.

In addition to the safety sensor or sensors 616, the design of the enclosure also prevents the escape of UV light from the enclosure. The design and location of both the collection aperture 150 and discharge aperture 138 in relation to the UV light source 630 help to prevent any UV light from escaping or emitting outside of the enclosure. Further, plastic doors may be attached in a hinged opening fashion to both the collection aperture 150 and discharge aperture 138 to provide additional UV protection.

In the alternative, an illumination switch 614 may be provided on sanitizer 100 which when activated, the processor 620 will instruct the irradiation of the UV light source 630 until the inner compartment of the sanitizer 100 is sanitized. When it has been determined that the writing utensils are sanitized, the processor 620 will instruct the UV light source 630 to cease operation.

The circuit includes controls for the drive motor assembly 130 which may be controlled in a variety of different ways, including in response to any of a variety of alternate activation mechanisms 612 and/or the input switch 610. One such example activation mechanism 612 may comprise a motion or proximity sensor, such that if the user motions his hand contemporaneously close to the activation mechanism 612 proximate to the discharge aperture 138 located outside of the writing utensil sanitizer 100, the circuit will receive a control signal to dispense a writing utensil. Employing a motion sensor enables a user to operate sanitizer 100 and obtain a sanitized implement without the need to physically touch sanitizer 100. This alternative embodiment is particularly advantageous where sanitizer 100 is used to sanitize eating utensils.

Another example activation mechanism 612 may comprise a signal receiver configured to receive a signal from a point of sale ("POS") device, such as POS device 410 and/or 510 described in more detail below. This alternate embodiment is particularly advantageous where sanitizer 100 is used to sanitize writing utensils and/or styluses. According to this alternate embodiment, a POS device sends a signal at an appropriate point while processing a transaction. The signal causes sanitizer 100 to dispense a writing utensil or stylus for the user to complete a POS transaction.

Other examples of activation mechanisms include a touch sensor, a motion sensor, a button that may be repressed and/or any other mode for activating a switch now known or later discovered in accordance with this invention.

Regardless of the embodiment, the activation mechanism 612 causes the processor 620 to instruct the power supply 628 to provide a source of power to drive motor assembly 130 to operate until a writing utensil is dispensed.

In the alternative, the drive motor assembly 130 may be instructed to cycle once and dispense a writing utensil in response to activation of the input switch 610. For example, if activation is sensed when a writing utensil 102a is inserted into the collection opening 150 or through activation mechanism 612, the processor 620 may issue an instruction to cycle the drive motor assembly 130 to dispense a writing utensil. The writing utensil may be dispensed before or after the UV light source 630 is activated to irradiate the various writing utensils. If, however, the only writing utensil in the sanitizer 100 is the one recently deposited, the processor 620 will sanitize the writing utensil before it is dispensed for use.

It should be noted that the processor 620 may be preferably implemented as a central processor section having overall, system-level control, to performing various computations, functions and other processes related to the sanitizer 100. The various components in the control circuit associated with the processor 620 can be implemented as a single microprocessor circuit or a plurality of separate dedicated or programmable integrated or other electronic circuits or devices, e.g., hardwired electronic or logic circuits such as discrete element circuits or programmable logic devices. The control circuit may include other circuitry or components, such as memory devices, relays, mechanical linkages, communications devices, etc., to affect desired control and/or input/output functions from various interfaces, such as where display 624 is an input/output interface. The sanitizer 100 may include more than one controller for the various electronic components in accordance with this invention.

Programmable memory may be provided to receive and store the various data information and can also store one or more computer readable control routines used by the processor 620 to operate the writing utensil sanitizer 100. The memory can be implemented using any appropriate combination of alterable, volatile or non-volatile memory or non-alterable, or fixed, memory. The alterable memory, whether volatile or non-volatile, can be implemented using any one or more of static or dynamic RAM, floppy disk and disk drive, writable or re-writable optical disk and disk drive, hard drive, flash memory or the like. Similarly, the non-alterable or fixed memory can be implemented using any one or more of ROM, PROM, EPROM, EEPROM, an optical ROM disk, such as CD-ROM or DVD-ROM disk, and disk drive or the like.

Figure 4:
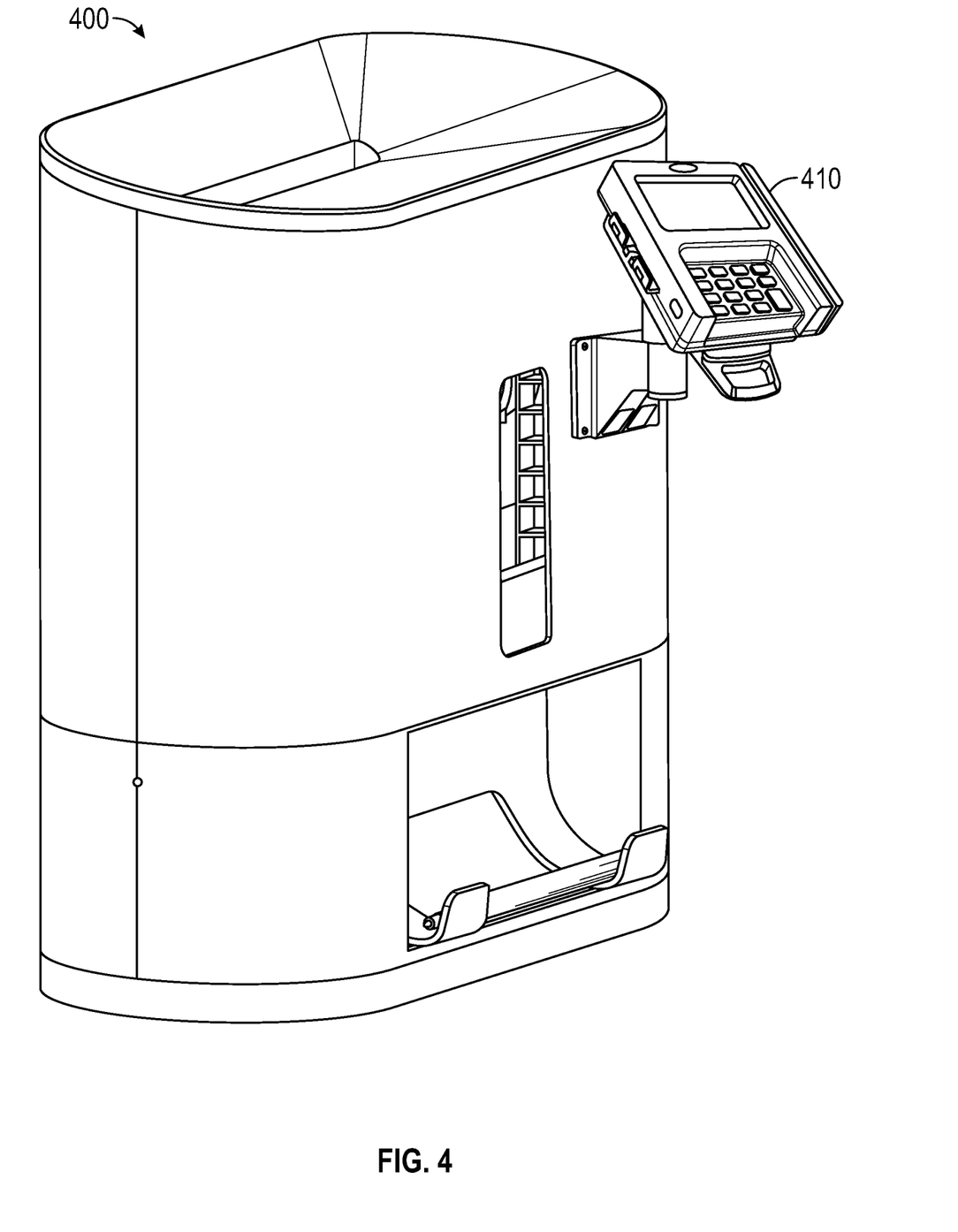
FIG. 4 illustrates a perspective view of a second example sanitizer system in accordance with this application.

Referring now to FIG. 4, there is illustrated a perspective view of a second example sanitizer 400. Sanitizer 400 comprises an integrated point of sale processing device 410. Integrated POS device 410 may act as an activation mechanism 612 as described herein above. Alternatively, it may act as a signal transmitter to an activation mechanism 612 that comprises a signal receiver.

Figure 5:
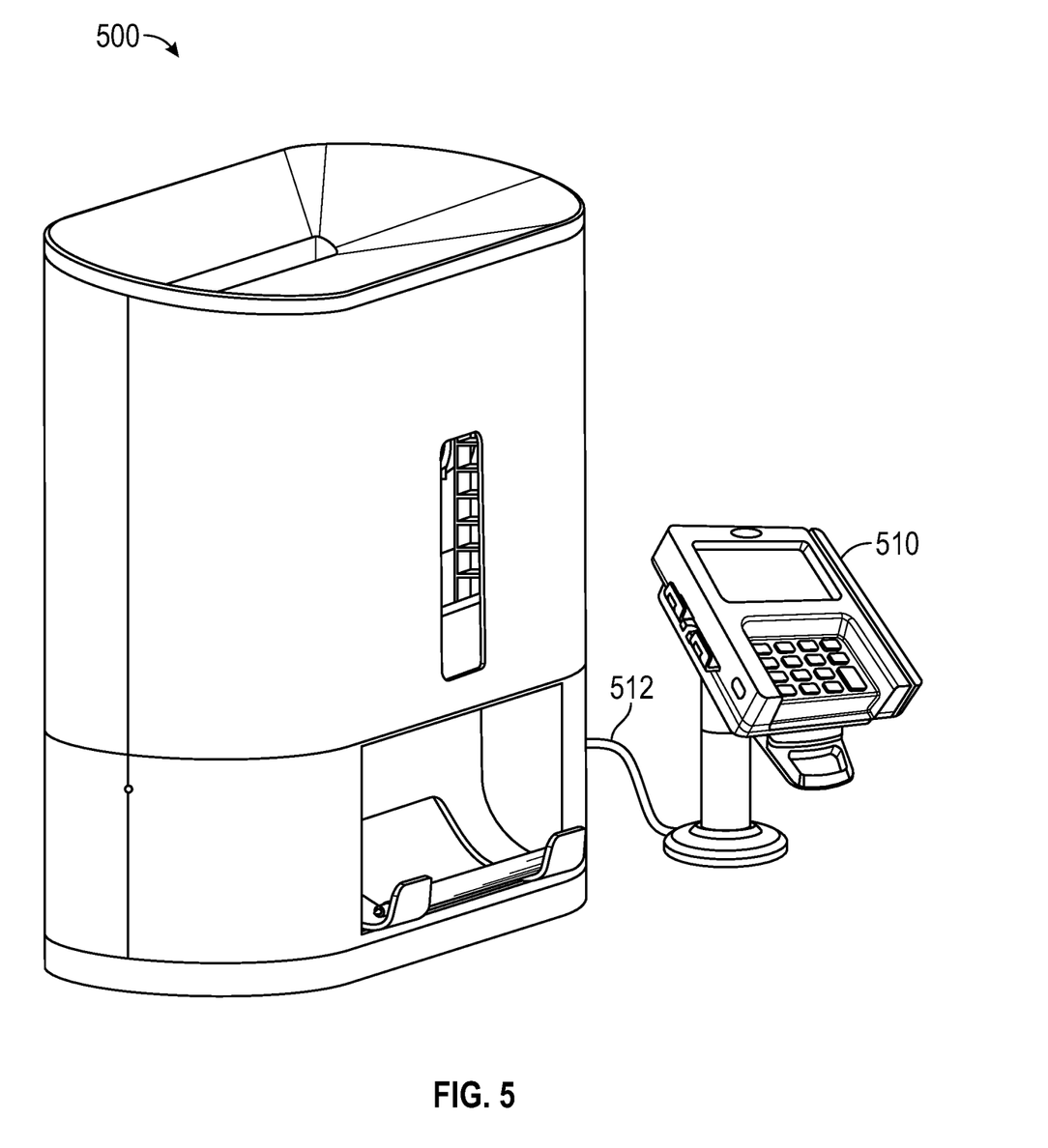
FIG. 5 illustrates a perspective view of a third example sanitizer system in accordance with this application.

Referring now to FIG. 5, there is illustrated a perspective view of a third example sanitizer 500. Sanitizer 500 is part of a system including a separate point of sale processing device 510. Separate POS device 510 may act as an activation mechanism 612 as described herein above. Alternatively, it may act as a signal transmitter to an activation mechanism 612 that comprises a signal receiver. In either embodiment, control signals are transmitted between POS processing device 510 and sanitizer 500 by means of cable 512.

While the systems, methods, and so on have been illustrated by describing examples, and while the examples have been described in considerable detail, it is not the intention of the applicant to restrict, or in any way, limit the scope of the appended claims to such detail. It is, of course, not possible to describe every conceivable combination of components or methodologies for purposes of describing the systems, methods, and so on provided herein. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

Finally, to the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995).

What is claimed is:

1. A sanitizer, comprising:
   a collection frame comprising a collection opening configured to receive an elongated implement;
   a discharge frame configured to dispense the elongated implement;
   an implement receiver, the implement receiver being a notched cylinder;
   a carrier system comprising a motor operative to drive a plurality of carrier belts, each carrier belt comprising a plurality of holders, the plurality of carrier belts disposed to receive the elongated implement from the implement receiver into one holder of each carrier belt, and the motor drives the plurality of carrier belts to transport the elongated item to the discharge frame;

an illumination source that sanitizes the elongated item by emitting radiation to the surface of the elongated item while it is transported by the carrier system;

at least one rotation belt, at least a portion of the at least one rotation belt being disposed above the plurality of carrier belts so that the elongated item rests on the at least one rotation belt, the at least one rotation belt configured to rotate the elongated object so that all sides of the elongated object are exposed to radiation from the illumination source; and at least one frame element supporting the carrier system, the at least one frame element configured to maintain the cooperative relationship of the carrier system and the at least one rotation belt.

2. The sanitizer of claim 1 further comprising a housing having a reflective inner surface that reflects the radiation of the illumination source.

3. The sanitizer of claim 1 further comprising at least one reflector that reflects the radiation of the illumination source toward the elongated item while it is transported by the carrier system.

4. The sanitizer of claim 1 further comprising an integrated point of sale terminal, the integrated point of sale terminal configured to cause the sanitizer to dispense an elongated item at a predetermined step of a point of sale process.

5. The sanitizer of claim 4 wherein the elongated item is a stylus.

6. The sanitizer of claim 4 wherein the elongated item is a writing utensil.

7. The sanitizer of claim 1 further comprising an activation mechanism configured to receive an activation signal from a remote point of sale terminal, the activation mechanism operative to cause the sanitizer to dispense an elongated item at a predetermined step of a point of sale process.

8. The sanitizer of claim 1 wherein the elongated item is a pair of chopsticks.

9. A sanitizer, comprising:
a collection frame comprising a collection opening configured to receive an eating utensil;
a discharge frame configured to dispense the eating utensil;
an implement receiver, the implement receiver being a notched cylinder for receiving the eating utensil;
a carrier system comprising a motor operative to drive a plurality of carrier belts, each carrier belt comprising a plurality of holders, the plurality of carrier belts disposed to receive the eating utensil from the implement receiver into one holder of each carrier belt, and the motor drives the plurality of carrier belts to transport the eating utensil to the discharge frame; and
an illumination source that sanitizes the eating utensil by emitting radiation to the surface of the eating utensil while it is transported by the carrier system; and
at least one frame element supporting the carrier system, the at least one frame element configured to maintain the cooperative relationship of the carrier system to the collection frame, the illumination source, and the discharge frame.

10. The sanitizer of claim 9 further comprising a housing having a reflective inner surface that reflects the radiation of the illumination source.

11. The sanitizer of claim 9 further comprising at least one reflector that reflects the radiation of the illumination source toward the eating utensil while it is transported by the carrier system.

12. The sanitizer of claim 9 wherein the eating utensil is a pair of chopsticks.

13. A sanitizer, comprising:
a collection frame comprising a collection opening configured to receive a stylus;
a discharge frame configured to dispense the stylus;
an implement receiver, the implement receiver being a notched cylinder operative to receive the stylus;
a carrier system comprising a motor operative to drive a plurality of carrier belts, each carrier belt comprising a plurality of holders, the plurality of carrier belts disposed to receive the stylus from the implement receiver into one holder of each carrier belt, and the motor drives the plurality of carrier belts to transport the stylus to the discharge frame;
an illumination source that sanitizes the stylus by emitting radiation to the surface of the stylus while it is transported by the carrier system;
at least one frame element supporting the carrier system, the at least one frame element configured to maintain the cooperative relationship of the carrier system to the collection frame, the implement receiver, and the illumination source; and
an integrated point of sale terminal, the integrated point of sale terminal configured to cause the sanitizer to dispense the stylus at a predetermined step of a point of sale process.

14. The sanitizer of claim 13 further comprising a housing having a reflective inner surface that reflects the radiation of the illumination source.

15. The sanitizer of claim 13 further comprising at least one reflector that reflects the radiation of the illumination source toward the elongated item while it is transported by the carrier system.

* * * * *